US009498567B2

(12) United States Patent
Patel et al.

(10) Patent No.: US 9,498,567 B2
(45) Date of Patent: Nov. 22, 2016

(54) SYSTEMS AND METHODS FOR CONTROLLING THE RETURN PHASE OF A BLOOD SEPARATION PROCEDURE

(71) Applicant: FENWAL, INC., Lake Zurich, IL (US)

(72) Inventors: Amit J. Patel, Algonquin, IL (US); Samantha M. Planas, Wauconda, IL (US)

(73) Assignee: Fenwal, Inc., Lake Zurich, IL (US)

( * ) Notice: Subject to any disclaimer, the term of this patent is extended or adjusted under 35 U.S.C. 154(b) by 231 days.

(21) Appl. No.: 14/500,166

(22) Filed: Sep. 29, 2014

(65) Prior Publication Data

US 2016/0089486 A1    Mar. 31, 2016

(51) Int. Cl.
*A61M 1/38*    (2006.01)
*A61M 1/02*    (2006.01)
*A61M 1/36*    (2006.01)
(Continued)

(52) U.S. Cl.
CPC .............. *A61M 1/382* (2013.01); *A61M 1/029* (2013.01); *A61M 1/0231* (2014.02); *A61M 1/262* (2014.02); *A61M 1/30* (2013.01); *A61M 1/303* (2014.02); *A61M 1/305* (2014.02); *A61M 1/342* (2013.01); *A61M 1/3496* (2013.01); *A61M 1/3626* (2013.01); *A61M 1/3646* (2014.02); *A61M 1/3693* (2013.01); *A61M 1/38* (2013.01);
(Continued)

(58) Field of Classification Search
CPC .... A61M 1/30; A61M 1/303; A61M 1/0231; A61M 1/029; A61M 1/262; A61M 1/301; A61M 1/306; A61M 1/342; A61M 1/3496; A61M 1/3603; A61M 1/3626; A61M 1/3643; A61M 1/3646; A61M 1/3693; A61M 1/3696; A61M 1/38; A61M 1/382; A61M 2202/0415; A61M 2202/0427; A61M 2205/12; A61M 2205/18; A61M 2205/3375; A61M 2205/3393; A61M 1/305
See application file for complete search history.

(56) References Cited

U.S. PATENT DOCUMENTS 5,529,685 A    6/1996  Irie et al.
6,261,065 B1   7/2001  Nayak et al.
(Continued)

FOREIGN PATENT DOCUMENTS

EP    0214803 A2    3/1987

OTHER PUBLICATIONS

European Search Report and Search Opinion for counterpart EP Appl. No. 15 18 7250, date of completion of the search Feb. 5, 2016.

*Primary Examiner* — John Kim
(74) *Attorney, Agent, or Firm* — Cook Alex Ltd.

(57) ABSTRACT

A method is provided for controlling the return phase of a blood separation procedure having a draw phase in which blood is drawn through an access or donor line, is separated, and a fluid, such as a cellular concentrate, is flowed into a reservoir, and a return phase in which fluid is flowed from the reservoir through the donor line. The method comprises flowing fluid from the reservoir through the donor line in a steady state return; monitoring the donor line for the presence of air; and, upon detecting air in the donor line, determining the amount of fluid remaining in the reservoir. Then, either i) the donor line is purged, if the amount of fluid remaining in the reservoir exceeds a predetermined amount, and the steady state return of fluid from the reservoir through the donor line is resumed; or ii) if the amount of fluid remaining in the reservoir does not exceed the predetermined amount, the return phase is ended by terminating the flow of fluid from the reservoir through the donor line.

7 Claims, 6 Drawing Sheets

(51) Int. Cl.
   *A61M 1/30*     (2006.01)
   *A61M 1/34*     (2006.01)
   *A61M 1/26*     (2006.01)

(52) U.S. Cl.
   CPC .. *A61M2205/18* (2013.01); *A61M 2205/3375* (2013.01); *A61M 2205/3393* (2013.01)

(56) References Cited

U.S. PATENT DOCUMENTS

| | | |
|---|---|---|
| 6,302,860 B1 | 10/2001 | Gremel et al. |
| 6,361,518 B1 | 3/2002 | Brierton et al. |
| 6,524,267 B1 | 2/2003 | Gremel et al. |
| 6,918,887 B1 | 7/2005 | Gremel et al. |
| 7,004,924 B1 | 2/2006 | Brugger et al. |
| 7,189,352 B2 | 3/2007 | Carpenter et al. |
| 7,198,751 B2 | 4/2007 | Carpenter et al. |
| 7,204,958 B2 | 4/2007 | Olsen et al. |
| 7,335,334 B2 | 2/2008 | Olsen et al. |
| 7,540,958 B2 | 6/2009 | Chevallet et al. |
| 7,563,240 B2 | 7/2009 | Gross et al. |
| 7,566,315 B2 | 7/2009 | Hirabuki |
| 7,608,053 B2 | 10/2009 | Felt et al. |
| 7,651,474 B2 | 1/2010 | Van Waeg et al. |
| 7,682,563 B2 | 3/2010 | Carpenter et al. |
| 7,686,779 B1 | 3/2010 | Gibbs |
| 7,740,800 B2 | 6/2010 | Olsen et al. |
| 7,819,834 B2 | 10/2010 | Paul |
| 7,824,356 B2 | 11/2010 | Wieting et al. |
| 7,829,018 B2 | 11/2010 | Olsen et al. |
| 7,922,683 B2 | 4/2011 | Ogihara et al. |
| 8,057,419 B2 | 11/2011 | Ellingboe et al. |
| 8,075,468 B2 * | 12/2011 | Min .................. A61M 1/3693 494/10 |
| 8,105,258 B2 | 1/2012 | Lannoy |
| 8,211,049 B2 | 7/2012 | Min |
| 8,366,649 B2 | 2/2013 | Ibragimov |
| 8,480,606 B2 | 7/2013 | Wieting et al. |
| 8,545,754 B2 | 10/2013 | Carpenter et al. |
| 8,628,489 B2 | 1/2014 | Pages et al. |
| 8,647,289 B2 | 2/2014 | Pages et al. |
| 8,684,959 B2 | 4/2014 | Paolini et al. |
| 8,685,258 B2 | 4/2014 | Nguyen et al. |
| 8,702,637 B2 | 4/2014 | Pages et al. |
| 8,877,063 B2 | 11/2014 | Kawarabata et al. |
| 8,894,600 B2 | 11/2014 | Kelly et al. |
| 8,939,926 B2 | 1/2015 | Wieting et al. |
| 8,956,317 B2 | 2/2015 | Rada |
| 2003/0009123 A1 * | 1/2003 | Brugger ............ A61M 1/3626 604/4.01 |
| 2005/0118059 A1 | 6/2005 | Olsen et al. |
| 2005/0234384 A1 | 10/2005 | Westberg et al. |
| 2005/0261619 A1 | 11/2005 | Gay |
| 2006/0089586 A1 | 4/2006 | Kaus et al. |
| 2009/0212070 A1 | 8/2009 | Johnson et al. |
| 2010/0089837 A1 | 4/2010 | Inoue et al. |
| 2010/0160137 A1 | 6/2010 | Scibona et al. |
| 2011/0040229 A1 | 2/2011 | Hannan et al. |
| 2011/0137224 A1 | 6/2011 | Ibragimov |
| 2014/0100506 A1 | 4/2014 | Pages et al. |
| 2014/0138294 A1 | 5/2014 | Fulkerson et al. |
| 2014/0148750 A1 | 5/2014 | Pages et al. |
| 2014/0174997 A1 | 6/2014 | Nimura et al. |
| 2014/0217020 A1 | 8/2014 | Meyer et al. |
| 2014/0217027 A1 | 8/2014 | Meyer et al. |
| 2015/0060362 A1 | 3/2015 | Pouchoulin |

* cited by examiner

SYSTEMS AND METHODS FOR CONTROLLING THE RETURN PHASE OF A BLOOD SEPARATION PROCEDURE

BACKGROUND

Field of the Disclosure

The invention relates to fluid separation systems and methods. More particularly, the invention relates to systems employing spinning membranes for fluid separation and methods for operating such systems.

Description of Related Art

Various blood processing systems now make it possible to collect particular blood constituents, instead of whole blood, from a blood source such as, but not limited to, a container of previously collected blood or other living or non-living source. Typically, in such systems, whole blood is drawn from a blood source, a particular blood component or constituent is separated, removed, and collected, and the remaining blood constituents are returned to the blood source. Removing only particular constituents is advantageous when the blood source is a human donor, because potentially less time is needed for the donor's body to return to pre-donation levels, and donations can be made at more frequent intervals than when whole blood is collected. This increases the overall supply of blood constituents, such as plasma and platelets, made available for transfer and/or therapeutic treatment.

Whole blood is typically separated into its constituents (e.g., red cells, platelets, and plasma) through centrifugation, such as in the AMICUS® separator from Fenwal, Inc. of Lake Zurich, Ill., or other centrifugal separation devices, or a spinning membrane-type separator, such as the AUTOPHERESIS-C® and AURORA® devices from Fenwal, Inc. Such separation devices typically comprise a fluid circuit having a separation chamber, sources or containers of various solutions, and collection containers that are interconnected by tubing and which is mounted onto a durable hardware component that includes pumps, clamps, and sensors that are automatically operated by a programmable controller to perform the desired blood separation procedure.

In the context of an apheresis procedure, in which whole blood is withdrawn from a donor or patient and a concentrated blood component is re-infused, certain efficiencies and enhancement of donor comfort and safety can be achieved if the draw and return phases of the procedure are divided into a series of sequentially-performed draw and return cycles. This causes the donor's blood volume to vary less over the course of the procedure, while maintaining the total volume of fluid withdrawn from and returned to the donor.

When the apheresis procedure is being performed with a single donor line that is used for both the draw and return phases of the procedure, the donor line must be cleared or primed prior to each commencement of the draw phase. In addition, during the return phase, if air is detected in the donor line, the return of fluid to the donor is suspended to permit purging air from the donor line, after which the return phase may be continued. By way of the present disclosure, a method is provided for performing the return phase of a blood separation procedure in which, in the case of air detection, the draw phase are may be immediately initiated, resulting in a more efficient performance of the procedure with reduced procedure time.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In a first aspect, a method is provided for controlling the return phase of a blood separation procedure having a draw phase, in which blood is drawn through an access or donor line, is separated and a fluid, such as a cellular concentrate, is flowed into a reservoir, and a return phase, in which fluid is flowed from the reservoir through the donor line. The method comprises flowing fluid from the reservoir through the donor line; monitoring the donor line for the presence of air; and, upon detecting air in the donor line, determining the amount of fluid remaining in the reservoir. Then either i) the donor line is purged if the amount of fluid remaining in the reservoir exceeds a predetermined amount (i.e., the reservoir is not substantially empty) and flow of fluid from the reservoir through the donor line is resumed, or ii) if the amount of fluid in the reservoir does not exceed the predetermined amount (i.e., the reservoir is substantially empty), ending the return phase by terminating the flow of fluid from the reservoir through the donor line.

In another aspect of the method, a subsequent draw phase is commenced upon termination of the flow of fluid from the reservoir through the donor line. Alternatively, the blood separation procedure may commence a procedure completion sequence upon the termination of the flow of fluid from the reservoir through the donor line at the end of the return phase, in which one or more of the following steps is performed: rinsing the fluid circuit, infusing the donor with saline, adding storage fluid to the collected component(s), transferring the collected component(s) to the final storage container(s), etc.

In a further aspect, the donor line is purged upon commencement of the draw phase.

In another aspect of the method, an air detector is associated with the donor line for monitoring the donor line for the presence of air.

In a further aspect of the method, the amount of fluid in the reservoir is determined by weighing the reservoir.

In another aspect, a blood processing system for processing whole blood or a whole blood component is provided in which the processing system includes a fluid flow circuit having a donor line and a reservoir in fluid communication with the donor line and a hardware component having an air detector associated with the donor line and a weigh scale (or equivalent) associated with the reservoir for determining the amount of fluid therein, and a controller with a user interface, the controller being configured to perform any of the methods described above.

DESCRIPTION OF THE ILLUSTRATED EMBODIMENTS

The embodiments disclosed herein are for the purpose of providing an exemplary description of the present subject matter. They are, however, only exemplary, and the present subject matter may be embodied in various forms. Therefore, specific details disclosed herein are not to be interpreted as limiting the subject matter as defined in the accompanying claims.

Figure 1:
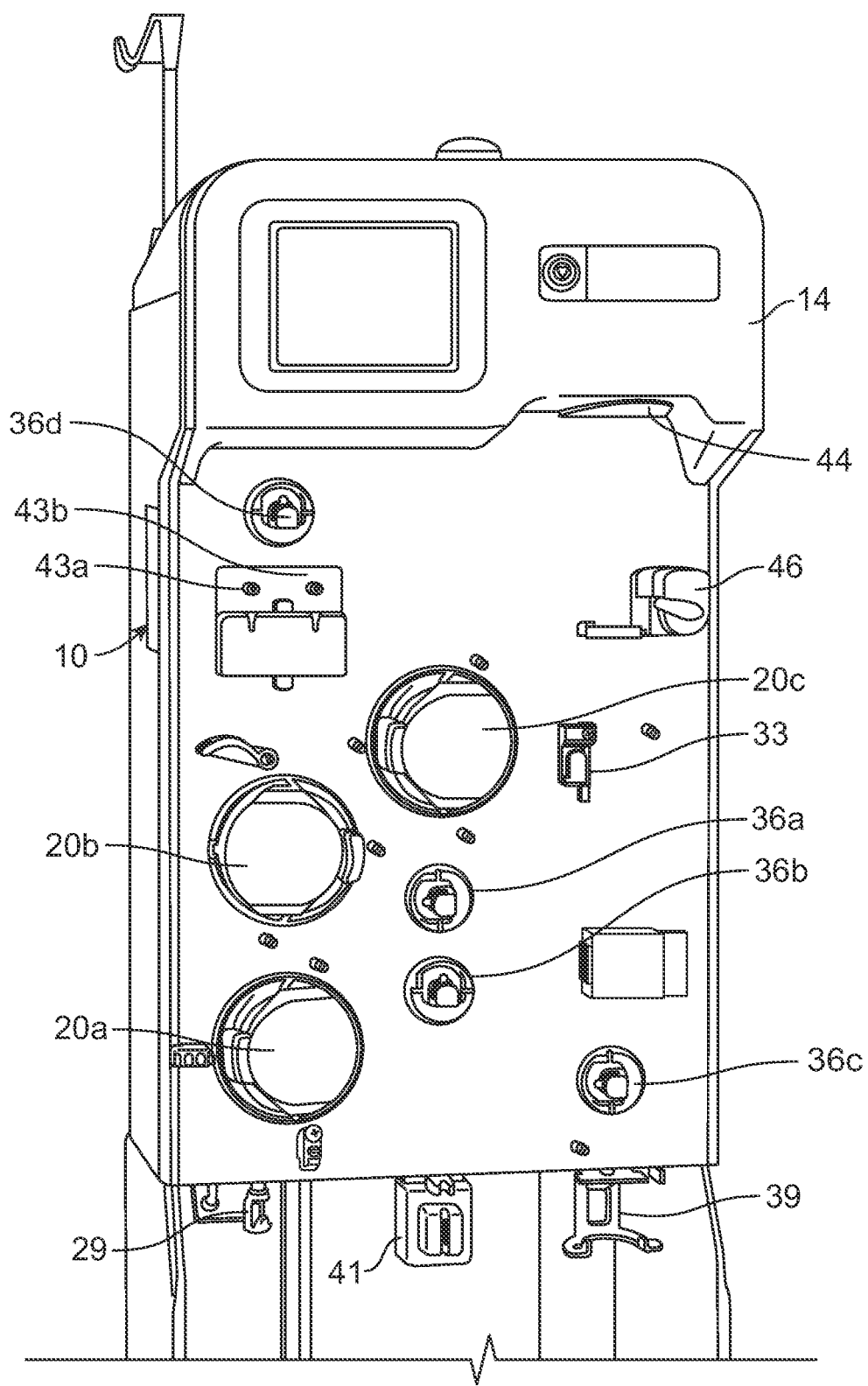
FIG. 1 is a front perspective view of an exemplary fluid separation system suitable for performing the method of the present disclosure.
Figure 2:
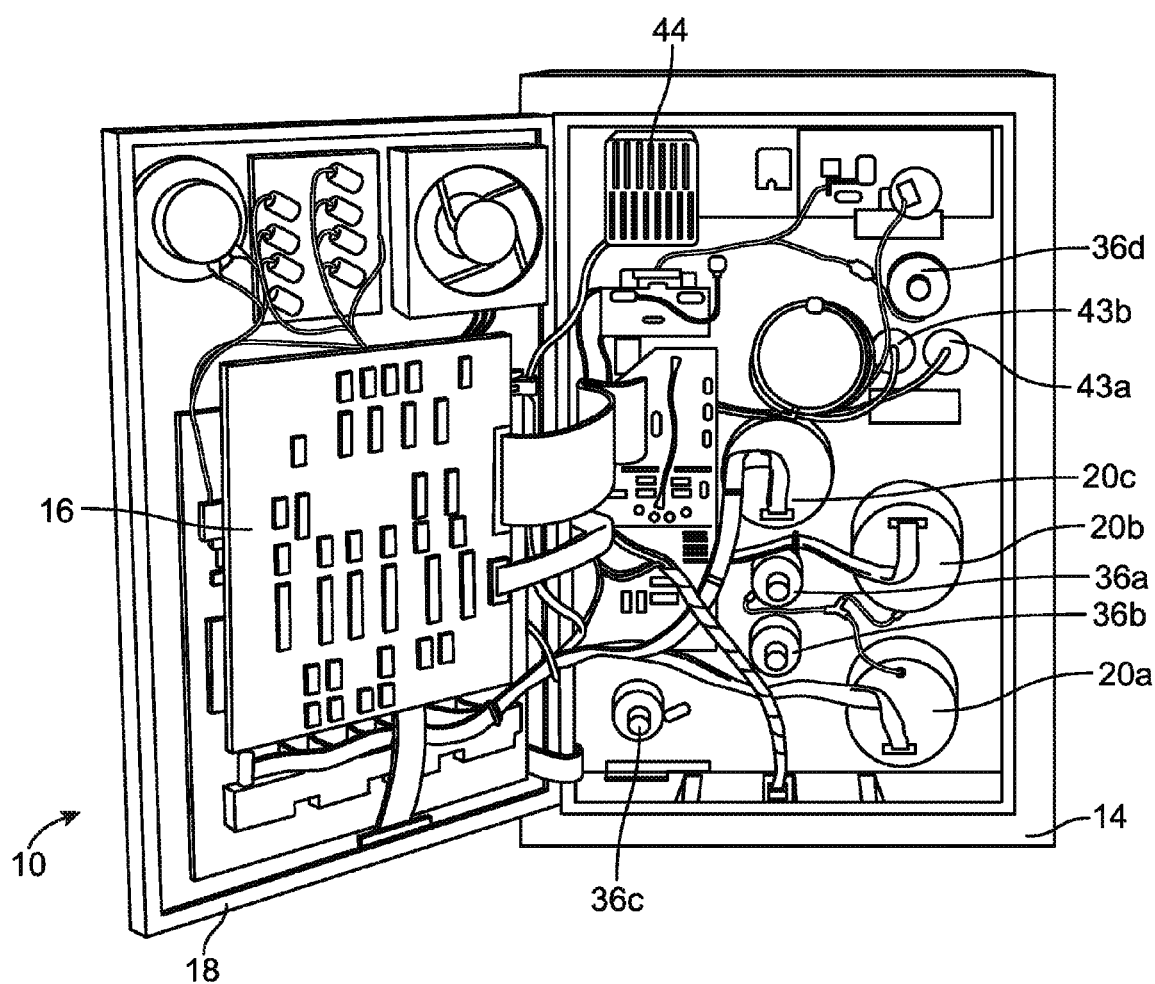
FIG. 2 is a rear perspective view of the fluid separation system of FIG. 1, with a rear door thereof in an open position.
Figure 3:
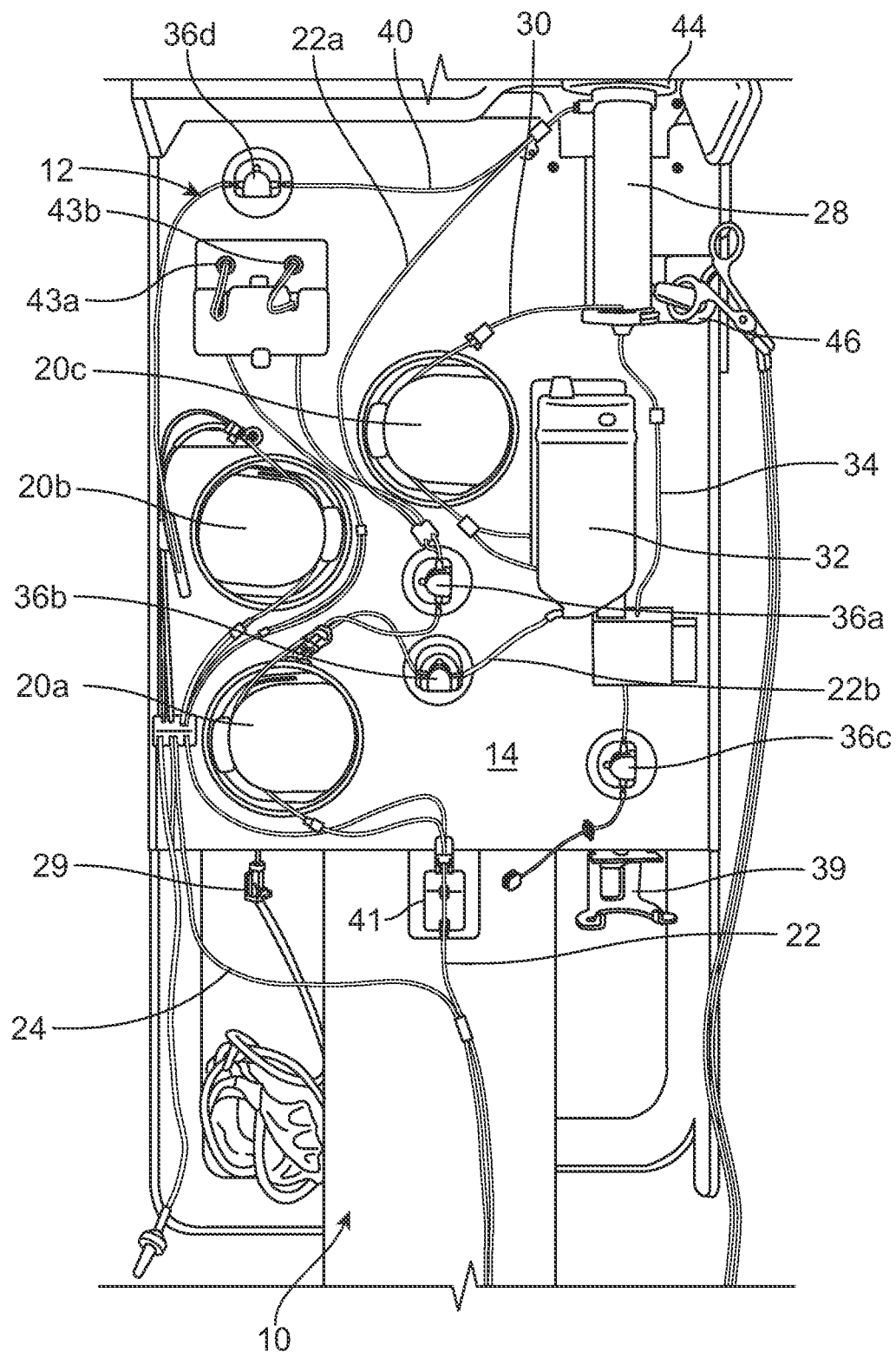
FIG. 3 is a front perspective view of the fluid separation system of FIG. 1, with a fluid flow circuit associated therewith.

According to an aspect of the present disclosure, a durable or reusable fluid separation system is used in combination with a separate fluid flow circuit (which may be disposable) to separate a fluid into two or more constituent parts. FIGS. 1 and 2 illustrate an exemplary fluid separation system 10, while FIG. 3 illustrates an exemplary fluid flow circuit 12 mounted onto the fluid separation system 10, but it should be understood that the illustrated fluid separation system 10 and fluid flow circuit 12 are merely exemplary of such systems and circuits and that differently configured fluid separation systems and fluid flow circuits may be provided without departing from the scope of the present disclosure.

Figure 5:
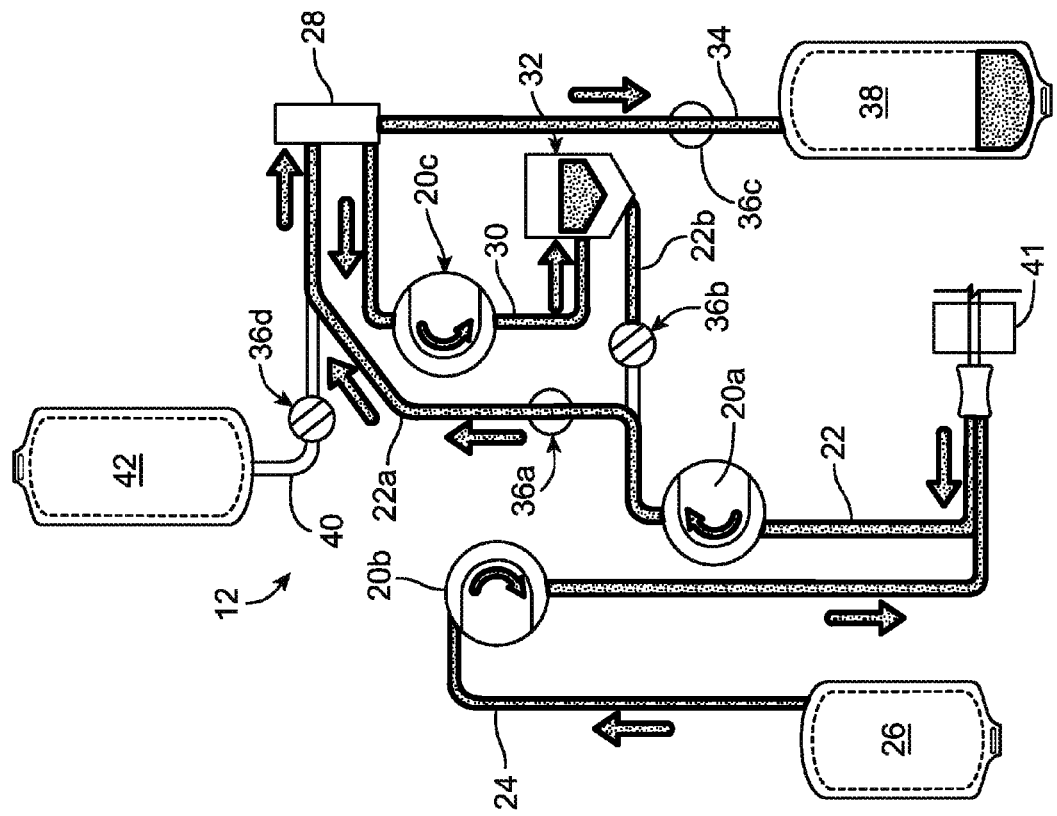
FIG. 5 is a schematic view of the fluid flow circuit and fluid separation system of FIG. 3, in a fluid draw mode.

The system 10 of FIG. 1 is configured for processing whole blood, but it may be used to process other biological fluids. The fluid may come from any fluid source during a draw or collection phase of the procedure (see, e.g., FIG. 5) and be returned to any recipient, which may be the same as or different from the fluid source, during a return or reinfusion stage (see, e.g., FIG. 6). In one embodiment, the fluid source/recipient is a living donor or patient (e.g., a human blood donor), while in other embodiments the fluid source and/or fluid recipient may be a non-living source/recipient (e.g., a blood bag or fluid container).

The illustrated system 10 includes a cabinet or housing 14, with several components positioned outside of the cabinet 14 (e.g., associated with a front wall or surface or panel of the cabinet 14) and additional components (including a programmable central processing unit or controller 16) and interconnects positioned inside of the cabinet 14, which may be accessed by opening a rear door 18 of the system 10, as shown in FIG. 2. Among the system components positioned on the outside of the cabinet 14, one or more pumps or pump stations 20a-20c may be provided, with the pumps 20a-20c configured to accommodate tubing lines of the fluid flow circuit 12.

One of the pumps 20a may be provided as a source/recipient access pump, which may be associated with a source/recipient access line 22 of the fluid flow circuit 12 (also referred to as a "donor line") and operates to draw fluid from a fluid source (FIG. 5) during the draw or collection phase, operates in reverse to return fluid to a fluid recipient (FIG. 6) during the reinfusion stage, and is stopped at the end of the reinfusion phase. Pump 20a also primes the fluid flow circuit 12 and clears air from the access line 22. Pump 20a may also be referred to herein as a "blood pump," as it serves to pump whole blood from its source (such as a donor or, in the case of previously collected blood, a container or reservoir) to the separation module or chamber 28, described below.

Another one of the pumps 20b may be provided as an anticoagulant pump, which may be associated with an anticoagulant line 24 of the fluid flow circuit 12 and operates to add anticoagulant from an anticoagulant source or container 26 of the fluid flow circuit 12 (FIG. 5) to fluid drawn from the fluid source in the source/recipient access line 22 before the fluid enters into a fluid separation module or chamber 28 of the fluid flow circuit 12. The anticoagulant container 26 is supported by a weigh scale hanger 29. Pump 20b does not, however, operate during the reinfusion phase of the procedure. Pump 20b may also be referred to herein as an "AC pump."

A third pump 20c may be provided as a return fluid pump, which may be associated with a return fluid outlet line 30 and operates to draw a return fluid (i.e., a fluid constituent to be returned to a fluid recipient) from the fluid separation chamber 28 and direct it into a return fluid reservoir 32 after the fluid has been separated into a return fluid and a collection fluid in the fluid separation chamber 28. The return fluid reservoir is supported by the weigh scale hanger 33. The pump 20c may also be used to prime the fluid flow circuit 12 and assist in clearing fluid from the fluid separation module 28 at the end of the procedure. Pump 20c does not, however, operate during the reinfusion phase of the procedure. Pump 20c may also be referred to herein as a "cell pump," as it serves to return cellular concentrate (i.e., concentrated red blood cells) to a donor in a plasmapheresis procedure.

In the illustrated embodiment, the pumps 20a-20c are peristaltic pumps, but it is within the scope of the present disclosure for differently configured pumps, such as diaphragm or other pumps, to be provided. Furthermore, additional or alternative pumps may be provided without departing from the scope of the present disclosure. For example, a pump may be associated with a collection fluid outlet line 34 of the fluid flow circuit 12 to draw a collection fluid from the fluid separation chamber 28 after the fluid from the fluid source has been separated into a return fluid and a collection fluid. Also, as will be described in greater detail herein, the illustrated embodiment employs a single fluid flow tubing or flow path for both drawing fluid from a source and flowing or returning it to a recipient, which are carried out intermittently. The system 10 could employ separate draw and return flow paths or tubes without departing from the scope of the present disclosure.

In addition to the pumps 20a-20c, the external components of the system 10 may include one or more clamps or valves 36a-36d associated with the tubing lines of the fluid flow circuit 12. The clamps or valves 36a-36d may be variously configured and operate to selectively allow and prevent fluid flow through the associated tubing line. In the illustrated embodiment, one clamp or valve 36a may be provided as a fluid source/recipient clamp, which may be associated with a draw branch 22a of the source/recipient access line 22 of the fluid flow circuit 12 to allow (FIG. 5) or prevent (FIG. 6) the flow of fluid through the draw branch 22a of the source/recipient access line 22. Another one of the clamps or valves 36b may be provided as a reinfusion clamp or valve, which may be associated with a reinfusion branch 22b of the source/recipient access line 22 downstream of a return fluid reservoir 32 of the fluid flow circuit 12 to allow (FIG. 6) or prevent (FIG. 5) the flow of return fluid through the reinfusion branch 22b. A third clamp or valve 36c may be provided as a collection fluid clamp or valve, which may be associated with the collection fluid outlet line 34 to allow (FIG. 5) or prevent (FIG. 6) the flow of collection fluid through the collection fluid outlet line 34 and into a collection fluid container 38, which is supported by the weigh scale hanger 39. A fourth clamp or valve 36d may be provided as a replacement fluid clamp or valve, which may be associated with a replacement fluid line 40 of the fluid flow circuit 12 to allow or prevent the flow of a replacement fluid out of a replacement fluid source 42 (e.g., a bag or container at least partially filled with saline). Additional or alternative clamps or valves may also be provided without departing from the scope of the present disclosure.

The illustrated system 10 further includes one or more pressure sensors 43a and 43b that may be associated with the fluid flow circuit 12 to monitor the pressure within one or more of the tubing lines of the fluid flow circuit 12 during operation of the pumps 20a-20c and clamps or valves 36a-36d. In one embodiment, one pressure sensor 43a may be associated with a tubing line that draws fluid from a fluid source and/or directs processed fluid to a fluid recipient, while the other pressure sensor 43b may be associated with a tubing line that directs fluid into or out of the fluid separation chamber 28 to assess the pressure within the fluid separation chamber 28, but the pressure sensors 43a and 43b may also be associated with other tubing lines without departing from the scope of the present disclosure. The pressure sensors 43a and 43b may send signals to the system controller 16 that are indicative of the pressure within the tubing line or lines being monitored by the pressure sensor 43a, 43b. If the controller 16 determines that an improper pressure is present within the fluid flow circuit 12 (e.g., a high pressure due to an occlusion of one of the tubing lines), then the controller 16 may instruct one or more of the pumps 20a-20c and/or one or more of the clamps or valves 36a-36d to act so as to alleviate the improper pressure condition (e.g., by reversing the direction of operation of one of the pumps 20a-20c and/or opening or closing one of the clamps or valves 36a-36d). Additional or alternative pressure sensors may also be provided without departing from the scope of the present disclosure. In addition, the system 10 preferably includes an air detector 41 associated with the donor line 22 to provide a signal to the controller 16 when air is detected in the donor line.

Figure 4:
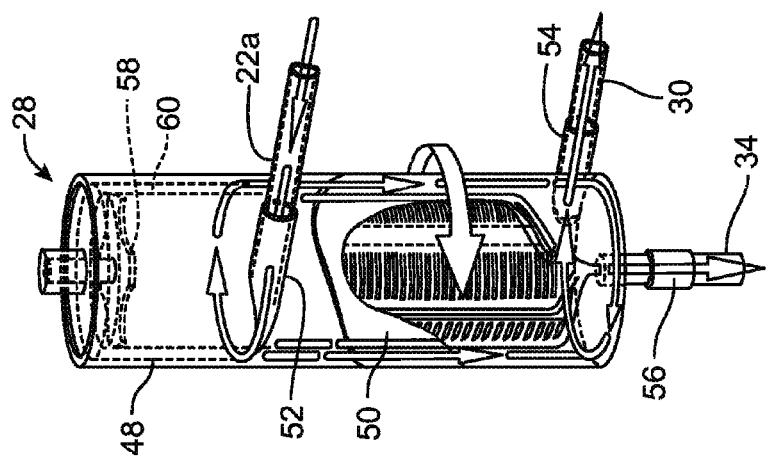
FIG. 4 is a front perspective view of a fluid separation chamber of the fluid flow circuit of FIG. 3, with a portion thereof broken away for illustrative purposes.

The system 10 may also include a separation actuator 44 that interacts with a portion of the fluid separation chamber 28 to operate the fluid separation chamber 28. A chamber lock 46 may also be provided to hold the fluid separation chamber 28 in place with respect to the system cabinet 14 and in engagement with the separation actuator 44. The configuration and operation of the separation actuator 44 depends upon the configuration of the fluid separation chamber 28. In the illustrated embodiment, the fluid separation chamber 28 is provided as a spinning membrane-type separator, such as a separator of the type described in greater detail in U.S. Pat. Nos. 5,194,145 and 5,234,608 or in PCT Patent Application Publication No. WO 2012/125457 A1, each of which is incorporated herein by reference. If provided as a spinning membrane-type separator, the fluid separation chamber 28 may include a tubular housing 48 (FIG. 4), with a microporous membrane 50 positioned therein. An inlet 52 allows a fluid from a fluid source to enter into the housing 48 (via the draw branch 22a of the source/recipient access line 22), while a side outlet 54 allows return fluid to exit the housing 48 (via the return fluid outlet line 30) and a bottom outlet 56 allows collection fluid to exit the housing 48 (via the collection fluid outlet line 34) after the fluid from the fluid source has been separated into return fluid and collection fluid.

In the illustrated embodiment, the separation actuator 44 is provided as a driver that is magnetically coupled to a rotor 58 on which the membrane 50 is mounted, with the separation actuator 44 causing the rotor 58 and membrane 50 to rotate about the central axis of the housing 48. The rotating rotor 58 and membrane 50 create Taylor vortices within a gap 60 between the housing 48 and the membrane 50, which tend to transport the return fluid away from the membrane 50 to exit the fluid separation chamber 28 via the side outlet 54, while the collection fluid passes through the membrane 50 toward the central axis of the housing 48 to exit the fluid separation chamber 28 via the bottom outlet 56. In one embodiment, whole blood from a blood source is separated into cellular blood components (return fluid) and substantially cell-free plasma (collection fluid). It should be understood that the present disclosure is not limited to a particular fluid separation chamber and that the illustrated and described fluid separation chamber 28 is merely exemplary. For example, in other embodiments, a differently configured spinning membrane-type fluid separation chamber may be employed (e.g., one in which the membrane 50 is mounted on an inside surface of the housing 48 or on both the rotor 58 and an inside surface of the housing 48 and facing the gap 60) without departing from the scope of the present disclosure.

The membrane 50 of the fluid separation chamber 28 may be variously configured without departing from the scope of the present disclosure. When the system 10 is to be used to separate blood into two or more constituents, at least a portion of the membrane 50 preferably has anti-thrombogenic characteristics to prevent or at least decrease the incidence of reaction, such as protein or platelet activation upon the blood being separated within the fluid separation chamber 28. As used herein, the term "anti-thrombogenic" is intended to refer to a substance or property characterized by an enhanced resistance to the accumulation of blood components than the materials typically employed in the manufacture of membranes of spinning membrane-type fluid separation chambers (e.g., nylon 6-6).

Any suitable membrane material (or combination of materials) and anti-thrombogenic material (or combination of materials) may be used in manufacturing the membrane 50. In one embodiment, the membrane 50 is formed of a polymeric material (e.g., nylon 6-6, polyethersulfone, polysulfone, polycarbonate, polyvinylidene fluoride, polyamide, or the like), with an anti-thrombogenic material (e.g., polyethylene glycol or any one of the additives or coatings provided by Interface Biologics, Inc. of Toronto, Canada, or the like) incorporated or mixed or blended therein. In another embodiment, the membrane 50 is fully formed from a polymeric material (e.g., nylon, polyethersuflone, polysulfone, polycarbonate, polyvinylidene fluoride, polyamide, or the like) and then an anti-thrombogenic material (e.g., polyethylene glycol, any one of the additives or coatings provided by Interface Biologics, Inc. of Toronto, Canada, or the like) is applied to or coated onto at least a portion of the formed membrane 50.

Figure 6:
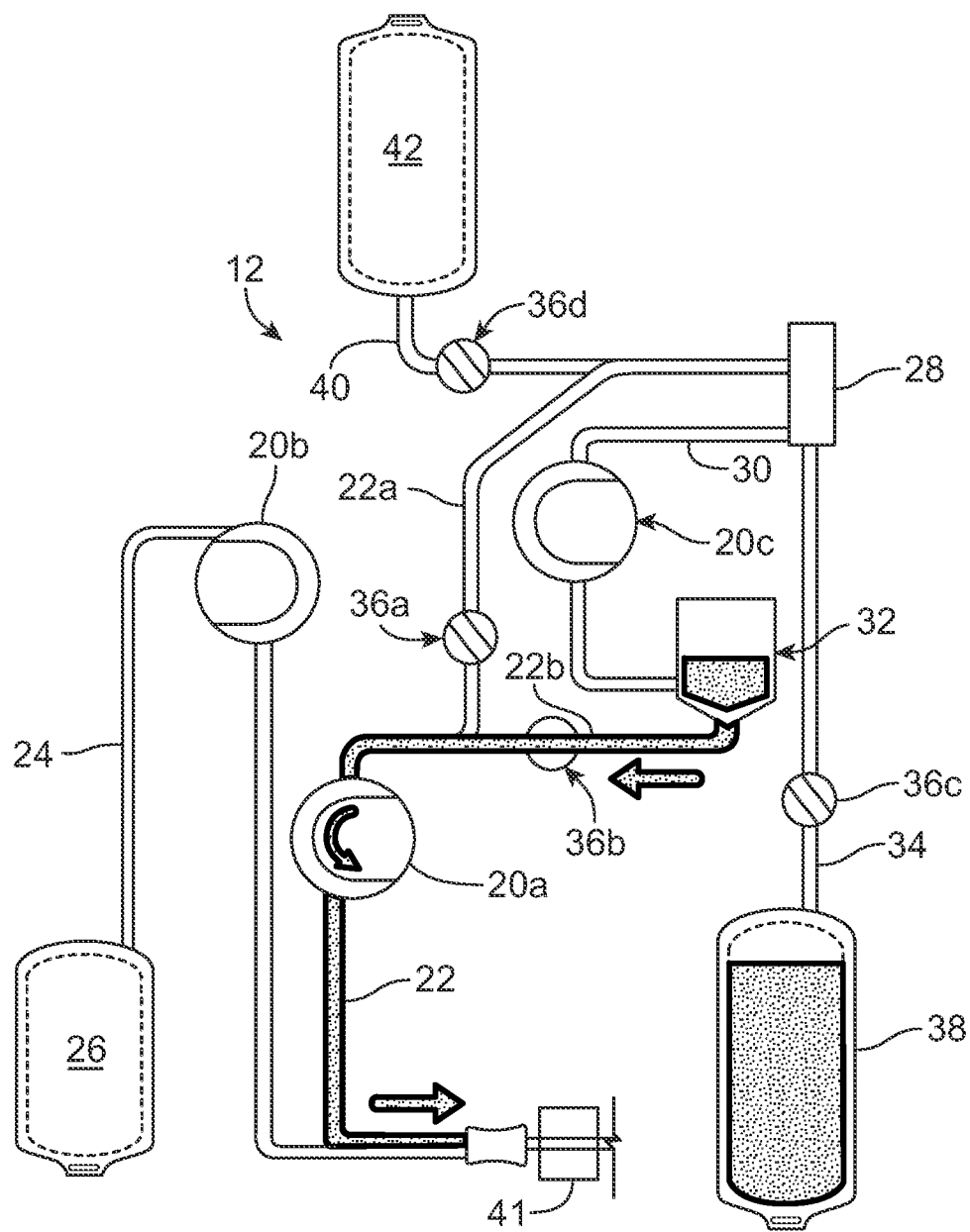
FIG. 6 is a schematic view of the fluid flow circuit and fluid separation system of FIG. 3, in a fluid return mode.

According to one method of using the fluid separation system 10 and fluid flow circuit 12, a fluid is drawn from a fluid source into the fluid separation chamber 28 during a draw or collection phase or mode (FIG. 5), where the fluid is separated into return fluid (e.g., concentrated cellular blood components) and collection fluid (e.g., substantially cell-free plasma). The collection fluid is retained by the system 10, while the return fluid is returned to the fluid source during a return or reinfusion phase or mode (FIG. 6). In one embodiment, the sequential performance of the draw and return phases (drawing from the fluid source, separating the fluid from the fluid source into return fluid and collection fluid, pumping the collection fluid to the fluid source or a different recipient, and returning the return fluid to the fluid source) are repeated until a target (e.g., a particular amount of collection fluid) is achieved. All of the draw phases and all of the return phases may be identical or may differ from each other. For example, a final draw phase may draw less fluid from the fluid source than the previous draw phases and a final return phase may infuse a combination of return fluid and replacement fluid to the fluid recipient, whereas the previous return phases pump only return fluid to the fluid recipient.

In accordance with the disclosure, a method is provided for controlling the return phase of a blood separation procedure having a draw phase, in which blood is drawn through the donor line, is separated and a cellular concentrate is flowed into a reservoir, and a return phase, in which cellular concentrate is flowed from the reservoir through the donor line.

Figure 7:
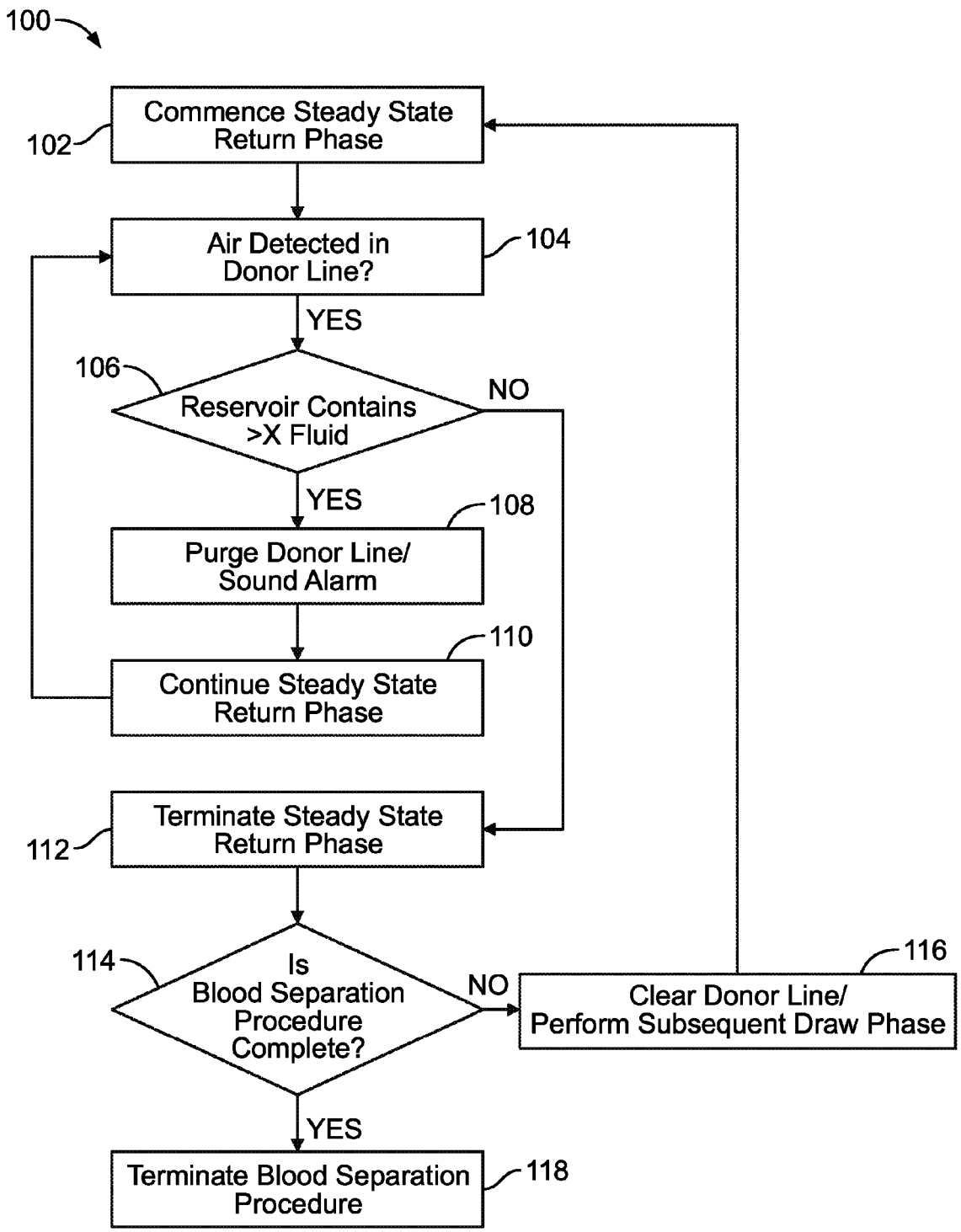
FIG. 7 is a flow chart schematically illustrating the various steps of the method of controlling the return fluid mode of the present disclosure.

Turning to FIG. 7, the steps of the method for controlling the return phase, generally designated 100, are schematically illustrated. As contemplated, the steps of the method are preferably automatically implemented by the system controller 16, described above. The method 100 has an initial step 102 commencing the steady state return phase by flowing the contents of the reservoir 34 (concentrated red blood cells, in the case of a plasmapheresis procedure) through the donor line 22. During the steady state return, the access or donor line 22 is monitored for the presence of air by way of, the air detector 41 associated therewith. If air is detected in the donor line, as indicated by step 104, pump 20a stops pumping, under control of the controller 16, in order to prevent air from reaching the donor. Then the amount of fluid remaining in the reservoir is determined, as indicated by step 106. The amount of fluid in the reservoir may be determined using the weigh scale 33. Alternatively, and without departing form the scope of the disclosure, optical sensors may be used to determine the amount of fluid in the reservoir, or the amount of fluid in the reservoir 34 may be determined based on the flow rates for pumps 20a and 20c that control the flow of fluid into and out of the reservoir.

Then, depending upon the amount of fluid remaining in the reservoir 34, one of two alternative steps is taken. If the amount of cellular concentrate remaining in the reservoir exceeds a predetermined amount, the operator is notified by, e.g. providing an audible and/or visible alarm, and then the donor line 22 is purged (with or without operator interaction), as indicated by step 108. The predetermined amount for which purging the air is performed may be any value greater than 0 mL, and in a non-limiting example is 50 mL. After purging the donor line of any air, the return phase of the procedure is resumed by continuing the flow of cellular concentrate from the reservoir 34 through the donor line, as indicated by step 110.

If the amount of cellular concentrate in the reservoir does not exceed the predetermined amount, then the return phase is terminated, as indicated by step 112, by terminating the flow of fluid from the reservoir through the donor line. The controller then determines whether the blood separation procedure is complete (i.e., whether the total desired amount of blood has been processed), as indicated by step 114.

If the total desired amount of blood has not been processed, the donor line is then cleared of cellular concentrate (and simultaneously purged of any air), and a subsequent draw phase is performed, as indicated by step 116. At the conclusion of the draw phase, a subsequent steady state return phase is commenced, in accordance with steps 102-114 set forth above.

If the blood separation procedure is complete (i.e., the total desired amount of blood has been processed, the controller then terminates the blood separation procedure, as indicated by step 118.

Thus, by way of the foregoing method, upon the reservoir being substantially empty, the donor line is purged/cleared only upon commencement of a subsequent draw phase. The donor line will not be unnecessarily purged upon the reservoir being substantially empty if the blood separation procedure is completed. Thus, procedure times are potentially reduced, and donor comfort and safety enhanced.

It will be understood that the embodiments and examples described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

Without limiting any of the foregoing, the subject matter herein may be found in one or more methods or apparatus. For example, in a first aspect, a method is provided for controlling the return phase of a blood separation procedure having a draw phase in which blood is drawn through an access or donor line, is separated, and a fluid, such as a cellular concentrate, is flowed into a reservoir, and a return phase in which fluid is flowed from the reservoir through the donor line. The method comprises flowing fluid from the reservoir through the donor line in a steady state return; monitoring the donor line for the presence of air; and, upon detecting air in the donor line, determining the amount of fluid remaining in the reservoir. Then, either i) the donor line is purged if the amount of fluid remaining in the reservoir exceeds a predetermined amount (i.e., the reservoir is not substantially empty), and the steady state return of fluid from the reservoir through the donor line is resumed; or ii) if the amount of fluid remaining in the reservoir does not exceed the predetermined amount (i.e., the reservoir is substantially empty) the return phase is ended by terminating the flow of fluid from the reservoir through the donor line.

In another aspect of the method, a subsequent draw phase is commenced upon termination of the flow of fluid from the reservoir through the donor line. Alternatively, the blood separation procedure may commence a procedure completion sequence upon the termination of the flow of fluid from the reservoir through the donor line at the end of the return phase.

In a further aspect, the donor line is purged upon commencement of the draw phase.

In another aspect of the method, an air detector is associated with the donor line for monitoring the donor line for the presence of air.

In a further aspect of the method, the amount of fluid in the reservoir is determined by weighing the reservoir.

In another aspect, a blood processing system for processing whole blood or a whole blood component is provided in which the processing system includes a fluid flow circuit having a donor line and a reservoir in fluid communication with the donor line and a hardware component having an air detector associated with the donor line and a weigh scale (or equivalent) associated with the reservoir for determining the amount of fluid therein, and a controller with a user interface, the controller being configured to perform any of the methods described above.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description, but is set forth in the following claims.

The invention claimed is:

1. In a blood separation procedure having at least a first and a second draw phase in which blood is drawn through a donor line, is separated and a fluid is flowed into a reservoir and a first return phase after the first draw phase in which fluid is flowed from the reservoir through the donor line, a method for controlling the first return phase of the procedure comprising:
   a) flowing fluid from the reservoir through the donor line;
   b) monitoring the donor line for the presence of air; and
   c) upon detecting air in the donor line, determining whether the amount of fluid remaining in the reservoir exceeds a predetermined amount and i) if the amount of fluid remaining in the reservoir exceeds a predetermined amount, purging the donor line and resuming flowing fluid from the reservoir through the donor line until the reservoir is substantially empty, or ii) if the amount of fluid in the reservoir does not exceed the predetermined amount, ending the first return phase by terminating flowing fluid from the reservoir through the donor line and commencing the second draw phase.

2. The method of claim 1 further comprising purging the donor line upon commencement of the second draw phase.

3. The method of claim 1 further comprising terminating the blood separation procedure upon the termination of the flow of fluid from the reservoir through the donor line.

4. The method of claim 1 in which an air detector is associated with the donor line for monitoring the donor line for the presence of air.

5. The method of claim 1 in which the amount of fluid in the reservoir is determined by weighing the reservoir.

6. The method of claim 1 in which the predetermined amount of fluid is greater than 0.0 mL.

7. A blood processing system for processing whole blood or a whole blood component, the processing system comprising a fluid flow circuit having a donor line and a reservoir in fluid communication with the donor line, and a hardware component having an air detector associated with the donor line, a weigh scale associated with the reservoir, and a controller with a user interface, the controller being configured to perform the method of claim 1.

* * * * *